Figure 1:
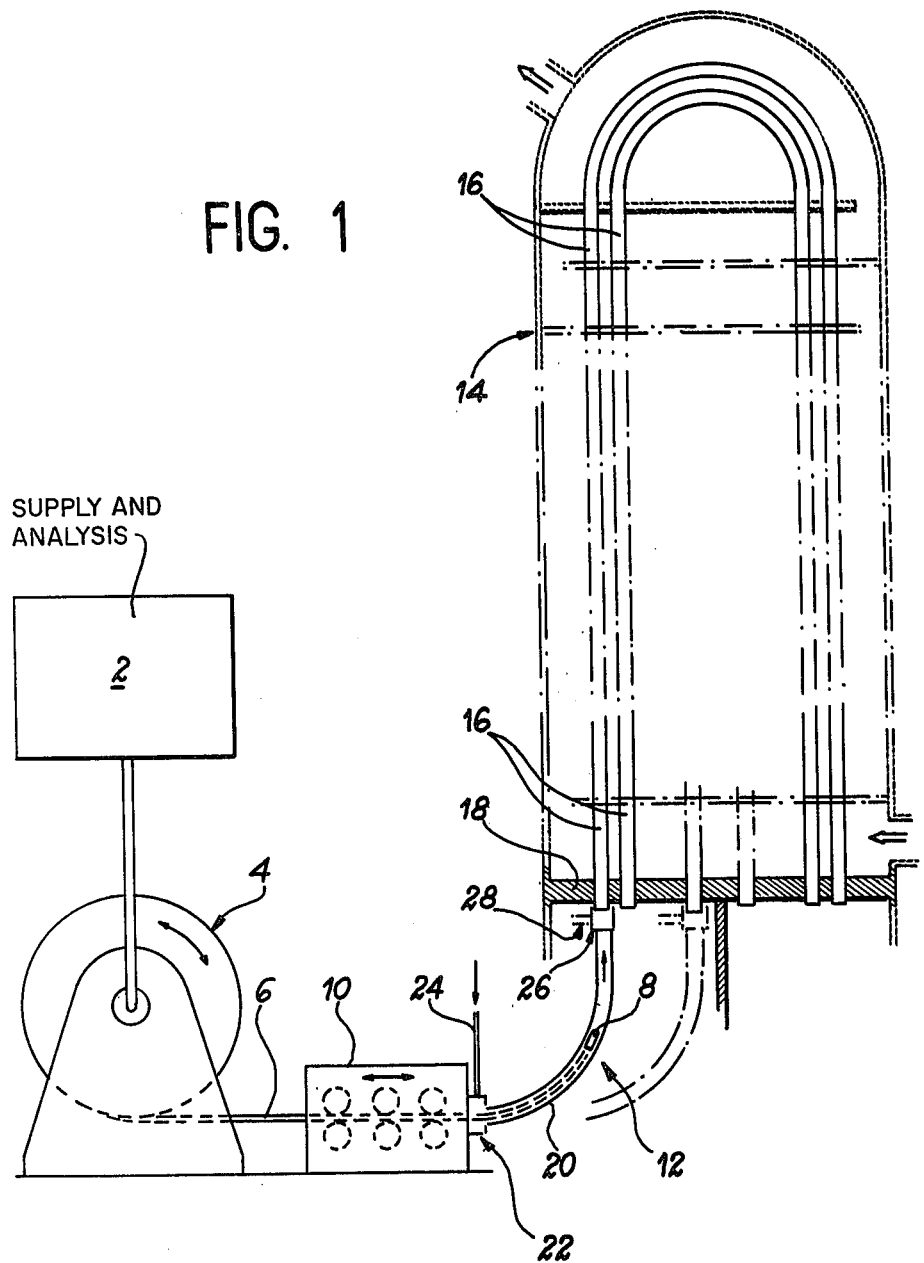

United States Patent [19]

Pigeon et al.

[11] 4,087,748

[45] May 2, 1978

[54] PNEUMATIC DRIVE DEVICE FOR A PROBE, PARTICULARLY AN EDDY CURRENT MEASURING PROBE

[75] Inventors: Michel Pigeon, Bures-sur-Yvette; Robert Saglio, Massy, both of France

[73] Assignee: Commissariat a l'Energie Atomique, Paris, France

[21] Appl. No.: 761,075

[22] Filed: Jan. 21, 1977

[30] Foreign Application Priority Data

Jan. 22, 1976 France .................................. 76 01728

[51] Int. Cl.² .......................................... G01R 33/12
[52] U.S. Cl. .................... 324/220; 324/238; 254/134.4
[58] Field of Search .................. 324/37, 40; 254/134.4

[56] References Cited

U.S. PATENT DOCUMENTS

| 526,141 | 9/1894 | Bloomer .............................. 254/134.4 |
| 2,470,338 | 5/1949 | Chilton .................................... 324/37 |
| 3,120,947 | 2/1964 | Hamrick ............................ 254/134.4 |
| 3,718,855 | 2/1973 | Rogel et al. ............................. 324/37 |
| 3,927,866 | 12/1975 | Linquist ............................ 254/134.4 |

FOREIGN PATENT DOCUMENTS

1,950,645 10/1969 Germany ........................... 254/134.4

Primary Examiner—Robert J. Corcoran
Attorney, Agent, or Firm—Cameron, Kerkam, Sutton, Stowell & Stowell

[57] ABSTRACT

A pneumatic drive device for a probe, more particularly for an eddy current measuring probe has a tight flexible tube in which the probe is movably mounted with a cable connected to the probe. A cable pushing and pulling device is connected to one end of the flexible tube and a compressed fluid is introduced into the flexible tube for driving the probe towards and then into the tube to be checked. A tight connection for the other end of the flexible tube to the tube to be checked is provided including a cylinder-piston-restoring spring assembly engaging the drive device beneath a tube to be checked and then disengaging the drive device from the tube which has been checked.

4 Claims, 4 Drawing Figures

PNEUMATIC DRIVE DEVICE FOR A PROBE, PARTICULARLY AN EDDY CURRENT MEASURING PROBE

The present invention has for its object a pneumatic drive device for a probe, particularly an eddy current measuring probe.

This device is characterised in that it comprises a tight flexible tube within which can move the probe connected to a cable, first means for connecting one of the ends of the flexible tube to a cable pushing and pulling device, means for introducing a compressed fluid into the flexible tube for driving the probe towards and then into the tube to be checked, and second means for the tight connection of the other end of the flexible tube to the tube to be checked, said second means comprising a cylinder-piston-restoring spring assembly making it possible to engage the drive device beneath a tube to be checked, and then disengage the said drive device from the tube which has just been checked.

Preferably, the cylinder-piston-restoring spring assembly comprises a rigid tube forming an extension of the flexible tube and in which the probe can be displaced, a cylinder around the said rigid tube defining a chamber which is supplied with compressed fluid, a piston which can be displaced in the said chamber under the action of the opposing thrust from the compressed fluid and the restoring springs, and a pipe for supplying said chamber with compressed fluid and which is branched on the pipe guiding the probe.

Advantageously these arrangements are combined with means for introducing a compressed fluid into the tube and which are constituted by a nozzle of the venturi type in the axis of which passes the cable connected to the probe. These means can be positioned in the means for connecting the flexible tube to the cable pushing and pulling device.

Figure 2:
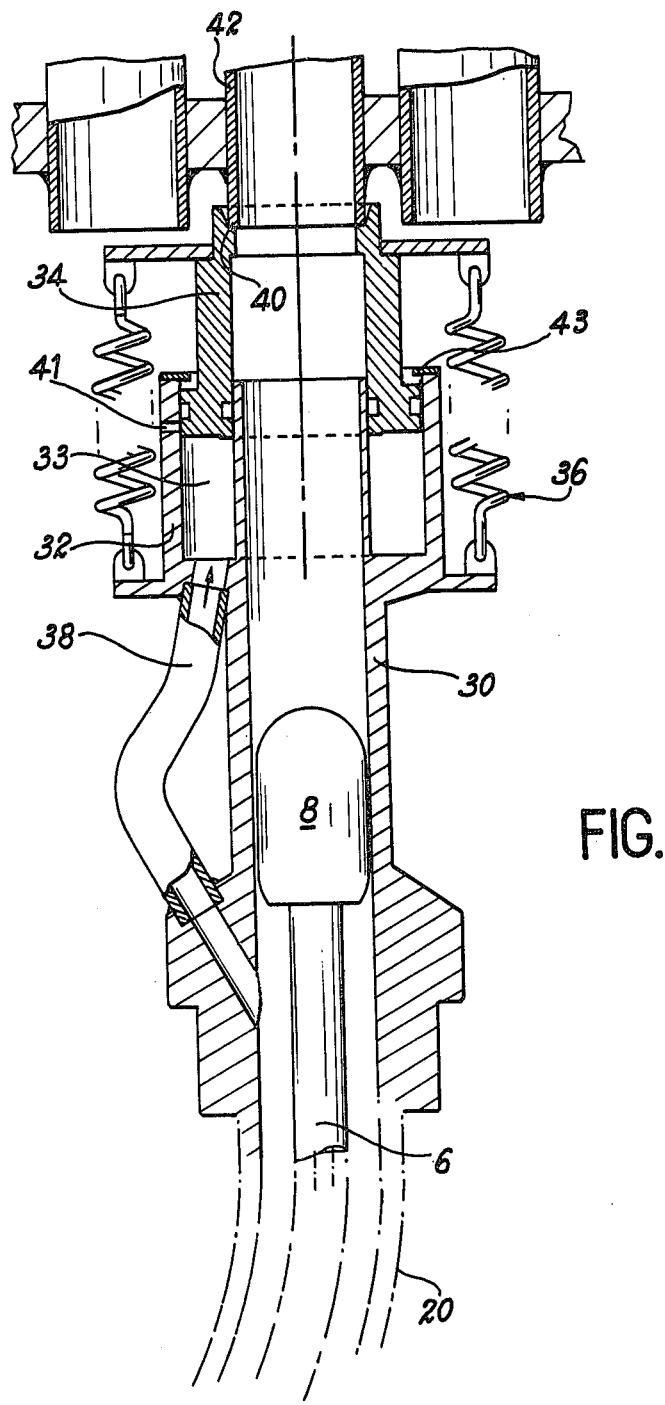
Figure 3:
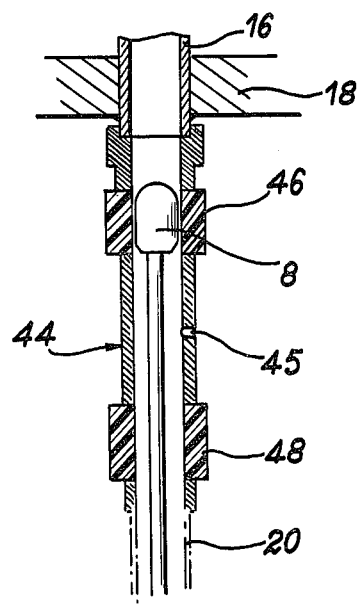
Figure 4:
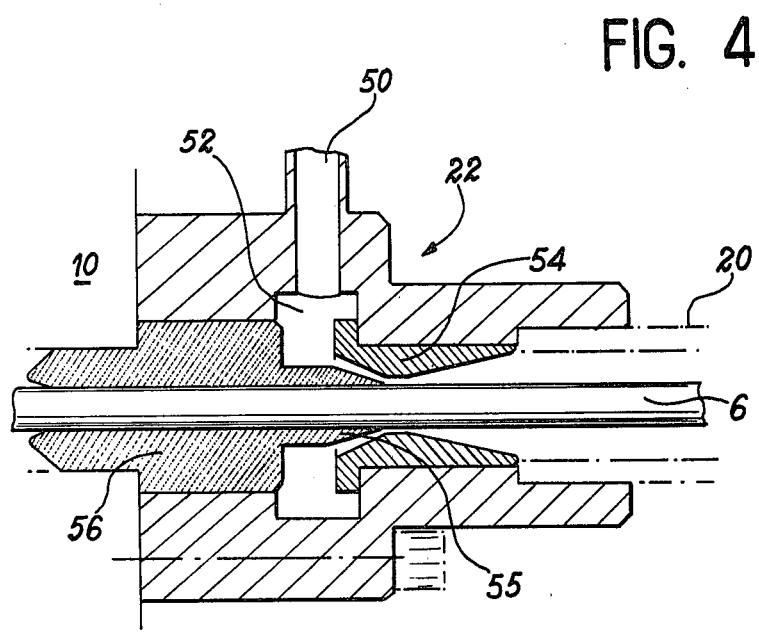

The characteristics and advantages of the invention can best be gathered from the following description of exemplified and non-limitative embodiments with reference to the attached drawings, wherein show:

FIG. 1, a general diagram of an installation for checking by means of eddy currents in which a probe can be displaced in a tube to be checked;

FIG. 2, a sectional view of means for connecting the flexible tube to the tube to be checked and illustrating more particularly the cylinder-piston-restoring spring assembly;

FIG. 3, schematically the use of members having special characteristics and a tube having at least one standard fault making it possible to check the calibration of the apparatus;

FIG. 4, a sectional view of the means for introducing compressed air into the flexible tube.

FIG. 1 schematically shows an installation for checking tubes by means of eddy currents. This installation comprises supply and analysis means 2, a cable reel 4, a cable 6 at the end of which is fixed a probe 8, a pushing and pulling device 10 permitting the displacement of the cable and the probe, a pneumatic drive device 12 forming the object of the present invention, an installation 14 comprising one or several tubes 16 which are to be inspected or checked. In the special case illustrated in FIG. 1 the installation 14 is a steam generator comprising U-shaped tubes fixed to a tube plate 18.

The device 12 for pneumatically driving the probe and which forms the object of the present invention comprises a tight flexible tube 20 within which can be displaced the probe 8 connected to cable 6, first means 22 for connecting one of the ends of the flexible tube 20 to the pushing and pulling device 10, means 24 for introducing compressed air into the flexible tube in order to drive the probe towards and then into one of the tubes 16 to be checked and second means 26 for connecting the other end of the flexible tube 20 to the tube to be checked 16.

These second means 26 can be integral with a positioning arm 28 controlled by a not shown but known device making it possible to displace the said means in order to bring them successively in front of the inlets of the different tubes to be checked.

The invention is substantially characterised in the fact that said second means 26 for connecting one end of the flexible tube to the tube to be checked comprise a cylinder-piston-restoring spring assembly making it possible to engage the end of the flexible tube beneath the tube to be checked in order to guide the probe there, and then to disengage the flexible tube from the said tube when it has been checked. These means are illustrated in greater detail in FIG. 2.

In FIG. 2 the cylinder-piston-restoring spring assembly comprises a rigid tube 30 forming an extension of the flexible tube 20 and in which can be displaced the probe 8, a cylinder 32 located around the said rigid tube 30 and defining a chamber supplied with compressed air, a piston 34 able to move in the chamber under the action of the opposing thrust of the compressed air supplying the chamber and the restoring springs 36 located between one of the ends of the piston and the base of the cylinder, and a pipe 38 for supplying chamber 33 with compressed air, said pipe being branched from the pipe which guides the probe.

This device functions in the following manner. A fraction of the compressed air introduced into tube 20 is diverted by pipe 38 towards chamber 33 when probe 8 has passed beyond the zone where pipe 38 is tapped on tube 20 (this situation is illustrated in FIG. 2). The pressure exerted by this compressed air on piston 34 has the effect of displacing the latter until it is applied to the lower end 40 of the tube to be checked 42. The probe guidance device is then connected to the tube to be checked and the probe, pushed by both the cable and the compressed air, penetrates said tube in order to carry out the inspection therein.

The compressed air flow is interrupted when probe 8 reaches the open end of the tube to be checked. The probe is then withdrawn from tube 42 by means of cable 6, pulled by means 10. When chamber 33 is no longer supplied by compressed air, piston 34 is drawn downwards by restoring springs 36 resulting in the disengagement of the device from the tube which has just been checked.

When the distance from the upper end of cylinder 32 from the lower end 40 of the tube exceeds the height of the chamber, the piston could leave the cylinder. To prevent this a stop 43 can be located at the end of the cylinder or an opening 41 can be made so as to permit compressed air to escape.

The pneumatic device according to the invention is particularly useful when the tubes which it is desired to check are placed at variable distances from the end of the probe guidance tube. The device according to the invention makes it possible to compensate height differences between the lower ends of the tubes to be checked. Moreover, the device according to the invention ensures the tightness of the guidance pipe during all the operations of connecting and forcing the probe 8 into the tubes to be checked.

The arrangements described hereinbefore are advantageously combined with means making it possible for reference signals to appear on the recording supplied by the electronic analysis means. These means can comprise, for example, a metallic tube portion having at least one known defect which serves as a standard defect. This is schematically shown in FIG. 3 where the metallic tube 44 has a defect 45, for example, a hole. Tube 44 can coincide with the rigid tube 30 of FIG. 2. When the probe detects this defect a signal of characteristic configuration appears on the control recording and this can be used for the calibration of the recording.

These means can also comprise zones 46 and 48 whose electrical conductivity and magnetic permeability are very different from those of the tube to be checked, being for example non-metallic and non-magnetic. The materials for each of the two zones can differ. Removable pieces can be used in place of zones 46 and 48 whereby when the probe passes into these zones, characteristic signals appear on the recording for the positioning the probe and for stopping or starting of the check by means of eddy currents. Optionally these signals can permit the determination of the displacement direction of the probe.

Zones 46 and 48 can, for example, comprise a plastic material and serve simultaneously as a connection between tubes 20 and 30 of FIG. 2.

If the tube is U-shaped, when the probe is withdrawn from the open end of the tube a characteristic signal appears associated with the fact that the probe is no longer surrounded by metallic material. This signal makes it possible to reverse the direction of movement of the probe and bring about the withdrawal thereof.

Obviously these members either having a standard fault or a characteristic signal can be positioned outside the means 26 for connecting the device to the tube to be checked and in more general manner at any point on the device.

The flexible tube of the device according to the invention is connected to a pushing and pulling device by means which can include, according to an advantageous variant, means serving to introduce compressed air into the flexible tube. This is illustrated schematically in FIG. 4.

FIG. 4 shows the means 22 for connecting the flexible tube to the pushing and pulling device 10 and which include compressed air introduction means constituted by a pressurised air supply pipe 50 issuing into a circular distribution chamber 52 which supplies a nozzle 54 in the form of a venturi. Lips 55 of member 56 are as close as possible to cable 6 but any friction is prevented. Moreover, a slight pressure reduction occurs upstream of the nozzle leading to a slight suction action. As a result of these arrangements contaminated dust which could come from the nuclear steam generator tubes cannot be blown to the outside of the flexible tube.

The above description of the invention shows that both as regards the connecting means to the pushing and pulling device and the connecting means to the tube to be checked, a perfect sealing is ensured for the probe drive device. This is one of the advantages provided by the invention which is of particular note when it is a question of checking or inspecting the tubes of an apparatus functioning more particularly in a nuclear reactor.

Obviously although the above description refers only to compressed air, this is only for explanatory purposes and any other fluid such as a gas or a liquid could also be used. It is also obvious that the device according to the invention could apply to any probe even if it is not of the eddy current type.

We claim:

1. A pneumatic drive device for a probe more particularly for an eddy current measuring probe, for driving said probe into a tube to be checked, comprising a tight flexible tube, a probe movable in said tube and connected to a cable, means for connecting one of the ends of said flexible tube to a pushing and pulling device for said cable, means for introducing a compressed fluid into said flexible tube between said pushing and pulling device and said probe to aid in driving said probe through said tube, and a cylinder-piston-restoring spring assembly at the other end of said flexible tube for connecting said tube to the tube to be checked comprising a rigid tube forming an extension of said flexible tube in which said probe can be moved, a cylinder around said rigid tube, said cylinder and said rigid tube defining a chamber, a piston movable in said chamber and adapted at one end to engage with the tube to be checked, a pipe connecting said chamber and said rigid tube to allow compressed fluid into said chamber and restoring springs between said piston and said cylinder, said compressed fluid engaging said piston beneath a tube to be checked and said restoring springs disengaging said piston from a tube which has been checked.

2. A device according to claim 1, wherein said rigid tube includes a metallic tube portion having at least one known standard defect.

3. A device according to claim 1, wherein said rigid tube includes at least a tube portion having electrical and magnetic characteristics very difference from those of the tube to be checked.

4. A device according to claim 1, wherein said means for introducing a compressed fluid into said flexible tube includes a nozzle of the venturi type in said means for connecting said flexible tube to said device for pushing and pulling the cable, said cable passing in the axis of said nozzle.

* * * * *